(12) United States Patent
Högberg et al.

(10) Patent No.: US 7,235,041 B2
(45) Date of Patent: *Jun. 26, 2007

(54) CENTRIFUGE FOR PROCESSING A BLOOD PRODUCT WITH A BAG SET HAVING A PROCESSING BAG

(75) Inventors: Niclas Högberg, Golden, CO (US); Emanuel Hällgren, Karlskoga (SE); Peter Pihlstedt, Stockholm (SE)

(73) Assignee: Gambro BCT, Inc., Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/461,593

(22) Filed: Aug. 1, 2006

(65) Prior Publication Data

US 2006/0270542 A1    Nov. 30, 2006

Related U.S. Application Data

(60) Continuation of application No. 10/627,029, filed on Jul. 24, 2003, now Pat. No. 7,097,774, which is a division of application No. 10/000,185, filed on Nov. 30, 2001, now Pat. No. 6,656,105, which is a continuation of application No. PCT/SE00/01076, filed on May 26, 2000.

(30) Foreign Application Priority Data

May 31, 1999    (SE) .................... 9901980

(51) Int. Cl.
 *B04B 7/12* (2006.01)
 *B04B 13/00* (2006.01)
(52) U.S. Cl. .............. 494/10; 494/23; 494/45
(58) Field of Classification Search ............ 494/1, 494/10, 23, 26–30, 42, 45, 47, 48, 84; 210/781, 210/782
See application file for complete search history.

(56) References Cited

U.S. PATENT DOCUMENTS 3,096,283 A    7/1963    Heln (Continued)

FOREIGN PATENT DOCUMENTS

DE    3815645    11/1989

(Continued)

OTHER PUBLICATIONS

A.H. Runck et al., *Continuous-flow Centrifugation Washing of Red Blood Cells*, Transfusion, vol. 12, No. 4, Jul.-Aug. 1972, pp. 237-244.

T.J. Contreras et al., *A Comparison of Methods to Wash Liquid-Stored Red Blood Cells and Red Blood Cells Frozen with High or Low Concentrations of Glycerol*, Transfusion, vol. 16, No. 6, Nov.-Dec. 1976, pp. 539-565.

International Search Report for PCT/SE00/01076, Sep. 28, 2000.

*Primary Examiner*—Charles E. Cooley
(74) *Attorney, Agent, or Firm*—Edna M. O'Connor; John R. Merkling; Laura B. Arciniegas

(57) ABSTRACT

A centrifuge for processing blood and blood components in a processing bag connected to at least one secondary bag comprises a rotor for spinning a processing bag and separating a content thereof in at least two components, and a squeezing member for exposing a processing bag to an external pressure and causing a transfer of a separated component from a processing bag into a secondary bag. Electrically powered devices, such as valves and photocells, are mounted on the rotor for controlling a transfer of fluid from a processing bag into a secondary bag. An electrical power supply system supplies the electrically powered devices with electrical power through the rotor.

13 Claims, 4 Drawing Sheets

U.S. PATENT DOCUMENTS

| | | |
|---|---|---|
| 3,145,713 A | 8/1964 | Latham, Jr. |
| 3,244,363 A | 4/1966 | Hein |
| 3,326,458 A | 6/1967 | Meryman et al. |
| 3,329,136 A | 7/1967 | Cadiou |
| 3,456,875 A | 7/1969 | Heln |
| 3,489,145 A | 1/1970 | Judson et al. |
| 3,519,201 A | 7/1970 | Eisel et al. |
| 3,600,900 A | 8/1971 | Buddecke |
| 3,679,128 A | 7/1972 | Unger et al. |
| 3,708,110 A | 1/1973 | Unger et al. |
| 3,724,747 A | 4/1973 | Unger et al. |
| 3,737,096 A | 6/1973 | Jones et al. |
| 3,858,796 A | 1/1975 | Unger et al. |
| 3,864,089 A | 2/1975 | Tiffany et al. |
| 3,885,735 A | 5/1975 | Westbert |
| 3,987,961 A | 10/1976 | Sinn et al. |
| 4,010,894 A | 3/1977 | Kellogg et al. |
| 4,016,828 A | 4/1977 | Maher, Jr. et al. |
| 4,111,355 A | 9/1978 | Ishimaru |
| 4,131,369 A | 12/1978 | Gordon et al. |
| 4,132,439 A | 1/1979 | Khoja et al. |
| 4,142,670 A | 3/1979 | Ishimaru et al. |
| 4,230,263 A | 10/1980 | Westberg |
| 4,244,513 A | 1/1981 | Fayer et al. |
| 4,268,393 A | 5/1981 | Persidsky et al. |
| 4,278,202 A | 7/1981 | Westberg |
| 4,303,193 A | 12/1981 | Latham, Jr. |
| 4,304,357 A | 12/1981 | Schoendorfer |
| 4,386,730 A | 6/1983 | Mulzet |
| 4,387,848 A | 6/1983 | Kellogg et al. |
| 4,388,184 A | 6/1983 | Brous et al. |
| 4,389,206 A | 6/1983 | Bacehowski et al. |
| 4,389,207 A | 6/1983 | Bacehowski et al. |
| 4,405,079 A | 9/1983 | Schoendorfer |
| 4,419,089 A | 12/1983 | Kolobow et al. |
| 4,421,503 A | 12/1983 | Latham, Jr. et al. |
| 4,439,177 A | 3/1984 | Conway |
| 4,447,221 A | 5/1984 | Mulzet |
| 4,459,169 A | 7/1984 | Bacehowski et al. |
| 4,482,342 A | 11/1984 | Lueptow et al. |
| 4,530,691 A | 7/1985 | Brown |
| 4,617,009 A | 10/1986 | Öhlin et al. |
| 4,720,284 A | 1/1988 | McCarty |
| 4,767,397 A | 8/1988 | Hohenberg et al. |
| 4,846,780 A | 7/1989 | Galloway et al. |
| 4,850,952 A | 7/1989 | Figdor et al. |
| 4,925,442 A | 5/1990 | Bodelson |
| 4,934,995 A | 6/1990 | Cullis |
| 4,936,820 A | 6/1990 | Dennehey et al. |
| 4,940,543 A | 7/1990 | Brown et al. |
| 4,990,132 A | 2/1991 | Unger et al. |
| 5,006,103 A | 4/1991 | Bacehowski et al. |
| 5,032,288 A | 7/1991 | Columbus et al. |
| 5,114,396 A | 5/1992 | Unger et al. |
| 5,160,310 A | 11/1992 | Yhland |
| 5,217,426 A | 6/1993 | Bacehowski et al. |
| 5,217,427 A | 6/1993 | Cullis |
| 5,316,540 A | 5/1994 | McMannis et al. |
| 5,368,542 A | 11/1994 | McMannis et al. |
| 5,571,068 A | 11/1996 | Bacehowski et al. |
| 5,593,378 A | 1/1997 | Dyck |
| 5,651,766 A | 7/1997 | Kingsley et al. |
| 5,674,173 A | 10/1997 | Hlavinka et al. |
| 5,704,887 A | 1/1998 | Slowik et al. |
| 5,723,050 A | 3/1998 | Unger et al. |
| 5,733,253 A | 3/1998 | Headley et al. |
| 5,759,147 A | 6/1998 | Bacehowski et al. |
| 6,261,217 B1 | 7/2001 | Unger et al. |
| 6,315,706 B1 | 11/2001 | Unger et al. |
| 6,348,031 B1 | 2/2002 | Unger et al. |
| 6,656,105 B2 * | 12/2003 | Hogberg et al. ............. 494/10 |
| 6,689,042 B2 * | 2/2004 | Unger et al. ............... 494/45 |
| 6,719,682 B2 * | 4/2004 | Kellogg et al. ............. 494/84 |
| 6,740,239 B2 | 5/2004 | Hogberg et al. |
| 6,835,171 B2 * | 12/2004 | Unger et al. ............... 494/27 |
| 6,852,074 B1 * | 2/2005 | Jorgenson et al. .......... 494/13 |
| 7,097,774 B2 * | 8/2006 | Hogberg et al. ........... 210/787 |
| 2002/0119880 A1 * | 8/2002 | Hogberg et al. ............. 494/5 |
| 2003/0195106 A1 * | 10/2003 | Kellogg et al. ............. 494/84 |
| 2004/0026341 A1 * | 2/2004 | Hogberg et al. .......... 210/782 |
| 2005/0045567 A1 * | 3/2005 | Holmes et al. ........... 210/782 |
| 2006/0270542 A1 * | 11/2006 | Hogberg et al. ............ 494/10 |

FOREIGN PATENT DOCUMENTS

| | | |
|---|---|---|
| DE | 4340678 A1 * | 6/1995 |
| EP | 0304431 | 3/1989 |
| EP | 0508474 A2 | 10/1992 |
| EP | 0508474 A3 | 10/1992 |
| EP | 0578086 | 1/1994 |
| EP | 0935966 | 8/1999 |
| EP | 1709983 A2 * | 10/2006 |
| FR | 8411225 | 1/1986 |
| GB | 1373672 | 11/1974 |
| SE | 35482 | 3/1973 |
| SE | 354581 | 3/1973 |
| WO | WO-85/02561 | 6/1985 |
| WO | WO-87/06844 | 11/1987 |
| WO | WO-87/06857 | 11/1987 |
| WO | WO-89/02273 | 3/1989 |
| WO | WO-92/00145 | 1/1992 |
| WO | WO-94/25086 | 11/1994 |
| WO | WO-95/01842 | 1/1995 |
| WO | WO-95/04591 | 2/1995 |
| WO | WO-96/29081 | 9/1996 |
| WO | WO-97/30715 | 8/1997 |
| WO | WO-98/35757 | 8/1998 |
| WO | WO-98/46362 | 10/1998 |
| WO | WO-01/02037 | 1/2001 |

* cited by examiner

CENTRIFUGE FOR PROCESSING A BLOOD PRODUCT WITH A BAG SET HAVING A PROCESSING BAG

This application is a continuation of U.S. application Ser. No. 10/627,029 filed Jul. 24, 2003, now U.S. Pat. No. 7,097,774, which is a division of U.S. patent application Ser. No. 10/000,185 filed Nov. 30, 2001, now U.S. Pat. No. 6,656,105 issued Dec. 2, 2003, which is a continuation of International Application No. PCT/SE00/01076 filed May 26, 2000.

FIELD OF INVENTION

The claimed invention relates to a centrifuge for processing blood and blood components and of which the function is based on an effective utilization of blood processing bags of ring type with associated, if required, secondary bags and other accessories. The secondary bags and the other accessories are of standard type within the area of technology and together these and the characteristic ring bags that are necessary for the centrifuge, in accordance with the invention, could be joined to the bag intended for various special blood processing purposes. This bag set, which is completely manufactured of inert plastic material allowing the blood and blood components to be seen, can therefore have different structures and designs depending on which type of blood processing they are intended for, but they are all based on the utilization of the ring bag as a basic component. The intention of the claimed invention is to offer a blood processing centrifuge with its special shape that makes it possible to limit the number of manual handling stages to a minimum, within every type of blood processing operation in which a centrifuging stage is included.

BACKGROUND

Different types of centrifuges intended for processing blood and blood components and also several types of ring bags intended for using in these centrifuges are to be found described in, for example, WO 87/06857, U.S. Pat. Nos. 5,114,396, 5,723,050, WO 97/30715, WO 98/35757. Of the centrifuges described therein it is primarily those that are included in the two latter-named patent documents that purpose-intended ring bags are utilized combined with standard secondary bags. In the blood processing bags that are stated in WO 87/06857 and in U.S. Pat. No. 5,114,396 instead of purpose-intended ring bags a more complicated type of bag is included, which consists of a ring formed blood processing chamber manufactured as one unit with a centrally arranged secondary bag. In U.S. Pat. No. 5,723,050 a further description is given of a ring bag intended for the same purpose which, in turn, is secured in a central assembly cover which, on the one hand, gives a central control of the ring bag and, on the other hand, to give room internally for the required secondary bags. In WO 97/30715 and WO 98/35757 it is indicated that the ring bags which are used during centrifuging are secured in the centrifuge by a number of holes on their periphery intended to be fitted over the pins secured in the centrifuge and which are intended for that purpose. This is all well and good but is not sufficiently good as has been shown during the course of the years. The stresses on the bags inner periphery edges, especially when it is only thin pins holding them in place, can be so excessive that the edges of the bags rupture.

SUMMARY OF THE INVENTION

To solve this problem the centrifuge, in accordance with the invention, has been equipped with a small number of, for example, three to five supports with a little larger diameter, divided at the same height as the intended position for the ring bag's inner periphery onto which the purpose-made guide holes along the ring bag's inner periphery are located. Via the support's greater contact line with the ring bag and by the centrifuge also being equipped with an opening and closing inner lid, which in the closed position clamps the ring bag's inner edge securely along and between the guide holes we have, in an effective way, been able to determine the ring bag's position in the centrifuge rotor and limit the stresses on the ring bag's inner edge. Consequently, the clamping function limits, through its greater contact area, the load on the ring bag's inner edge and prevents it from slipping over or, in some other way, being released from the supports while the centrifuging is activated. Apart from that, in the inner lid one or several photocells are advantageously arranged which after centrifuging are used for determining when emptying the ring bag shall be interrupted, in other words, when approaching the interface between the desired and the non-desired component.

By placing the previously described supports with less asymmetry and with the ring bags intended guide holes arranged in the same asymmetric way, a prior defined position for the ring bags is obtained automatically. This has several advantages as it is also possible to define the position for the tubes that connect the ring bags in the different bag sets with each respective secondary bag. We, of course, have found that we can utilize the thicker supports for some other purpose than just for holding the ring bags in position in the centrifuge. According to the claimed invention the supports can thus be equipped with built-in clamping instruments in which the different tubes between the ring bag and secondary bags can be arranged and with which the passage through these tubes can be opened and closed. Apart from that these clamp valves can, on condition that there is sufficient electric power via the centrifuge rotor, be combined with a cutting and welding function with which the tube which passes the clamp valve in question can be sealed and cut as soon as the connecting function, which it represents, is no longer needed. Another occasion when it simplifies how the ring bag is to be placed in the centrifuge is when the used bag set contains a cell trap for which there should suitably exist a preferred space in the centrifuge rotor or on its inner lid. A similar cell trap can, for example, be of the type that is described in WO 97/30715, which in principle consists of one on one priority defined arc in the slightly longer connecting tube in the centrifuge's rotating part.

That it is at all possible to weld requires, as previously indicated, access to electric power in the centrifuge's rotor and this problem has, in accordance with this further variant of the invention, been solved by means of an arranged slip-ring clutch along the centrifuge's rotor axle. Access to the slip-ring clutches that are concentrically arranged around the centrifuge's rotor axle and by which means access to the electric power in the centrifuge rotor has also made possible an effective program control of the different functions in the centrifuge.

A further improvement to the blood processing centrifuge, in accordance with the invention, relates to the production of medicinally valuable blood platelet plasma from the concentrate product, which is designated Buffy Coat at blood donor centers. Before the Buffy Coat can be centrifuged, making the blood platelet-rich product accessible, the original material, which is viscous, is diluted with a standard diluting solution. An example of a similar standard diluting solution that is used profusely in this area is generally designated T-Sol. In normal cases the Buffy Coat is available in the form of concentrates from previous extractions of red blood cells and plasma from whole blood. Each concentrate batch of Buffy Coat is, as a rule, too small, even after diluting with the relevant diluting solution, to be worth an individual centrifuging. As every similar type of Buffy Coat concentrate is initially available in its own blood processing bag a decided amount of diluting solution was previously manually added to each of a number of similar blood processing bags and shaken manually until an acceptable mixture resulted and added together to a larger bag which was centrifuged.

Apart from all manual handling and the related time required, there is a risk that the person who must shake the blood bags receiving neck and shoulder injuries in the long-term.

To be able to also mechanize this blood processing stage we have now, on the one hand, produced a special bag set intended for that purpose and which includes a ring bag, and on the other hand equipped the centrifuge, in accordance with the invention, with a special mixing function. In the design preferred by us of this part of the invention the mixing function has been built into or made securable to the outer lid of the centrifuge. In or on the outer lid there is a specially arranged small electrically powered motor. This motor has the special characteristic that it never makes a complete revolution in any direction but is quickly stopped before making a complete revolution and thereafter returns to a new incomplete revolution. The movement of +92.degree, lasting one or several minutes, has shown that it produces the mixing function we have endeavored to reach, which, will become evident, has as its prime task the replacement of the previous manual flushing of the Buffy Coat bags with the required amount of diluting solution, which, today, generally follows after the operation named Pooling. The special motor function is achieved by means of a gear box, crank function or by control of the motor. From a theoretical point of view the hydraulic motor could also be used for this purpose, even when taking into account a lower shaking speed and longer mixing time.

Connected to the aforementioned motor there is a cassette or holder in which the number of concentrate bags with Buffy Coat that are intended to be included in a process can be attached. Before these concentrate bags are attached to the cassette, they have been joined by sterile welding, via an own connecting tube, to the bag set intended for processing to which there is included a connecting tube with which all bags with Buffy Coat can be connected to a bag with the required amount of diluting solution, as well as via an other connecting tube to a ring bag and finally a connecting tube between the ring bag and a storage bag for the desired final product.

When extracting blood platelet plasma from the Buffy Coat the number of bags with the original material that is intended to be included in a centrifuging are connected via separate connecting tubes in each bag set. These connecting tubes are then in turn joined in a multi-way connector to which the diluting solution bag's connecting tube is also connected. The latter connecting tube is applied at the same time to a clamp valve on one of the centrifuge rotor's supports while the bags with Buffy Coat are attached to the aforementioned cassette and the bag with the diluting solution is suspended in the intended holder sufficiently high up for the desired amount of diluting solution to be able to be added to each respective Buffy Coat bag. The addition of the diluting solution to the Buffy Coat bags is then controlled by the aforementioned clamp valve, which, in turn, is controlled by a control program that is part of the centrifuge's control system, which also selects the time for starting the motor and the length of time it must be operated. It is most suitable to add the diluting solution in several portions with a motor operation between each addition. Resolving the Buffy Coat in the diluting solution is carried out without any manual shaking operation. As the motor operates the cassette with a special forwards and backwards movement we avoid the problem associated with damaging the various tubes. It is only the tube between the ring bag and the final product's storage bag that is not affected by the mixing operation. After the resolution of the Buffy Coat in the different original bags is finalized, the contents of all the bags are added to the ring bag included in the bag set via a separate connecting tube, which is also connected to the previously named multi-way connector and which, on its way to the ring bag, is placed in the clamp valve on another support by which this connection is controlled. After all substance has been transferred to the ring bag the connection between this and the original bags is interrupted and the diluting solution by sealing the relevant connecting tube on one of the centrifuge rotor's supports, which it passes, after which the empty bags and their connecting tubes can be rejected. After that a centrifuging of the diluting solution/ Buffy Coat mixture is carried out while the storage bag intended for the final product is allowed to lie in the centrifuge rotor's centre chamber. At the end of the centrifuging operation the lighter blood platelet product is transferred to the final storage bag. In connection with that the designed apparatus is utilized in a well-known way to expose the ring bag to an external pressure with which it can be emptied, to a greater or lesser degree. This apparatus consists of a membrane arranged under the ring bag, beneath which hydraulic fluid can be added and thereby expose the ring bag to an external pressure. When emptying the ring bag needs to be interrupted it is decided by one or several arranged photocells located in the centrifuge's outer lid which employ the difference in color between the light desired blood platelet's rich final product and the dark heavier concentrate products that are gathered along the outer periphery of the bag. When emptying the ring bag it is suitable to do this in a well-known way through the designed cell trap which, for example, can be of the type described in WO 97/30715. When the desired amount of blood platelet plasma is removed from the ring bag the connecting tube between the ring bag and the final storage bag is sealed in a well-known way whereby both ends of the tube are blocked. All that remains after that is to point out that the holder for the diluting solution bag and cassette for the Buffy Coat bags can be made removable, in order not to interfere with the centrifuge's other functions.

The invention has now been defined in its various functions in the following patent claims and they shall now be given a somewhat additional description relating to the attached figures.

DETAILED DESCRIPTION

Figure 1:
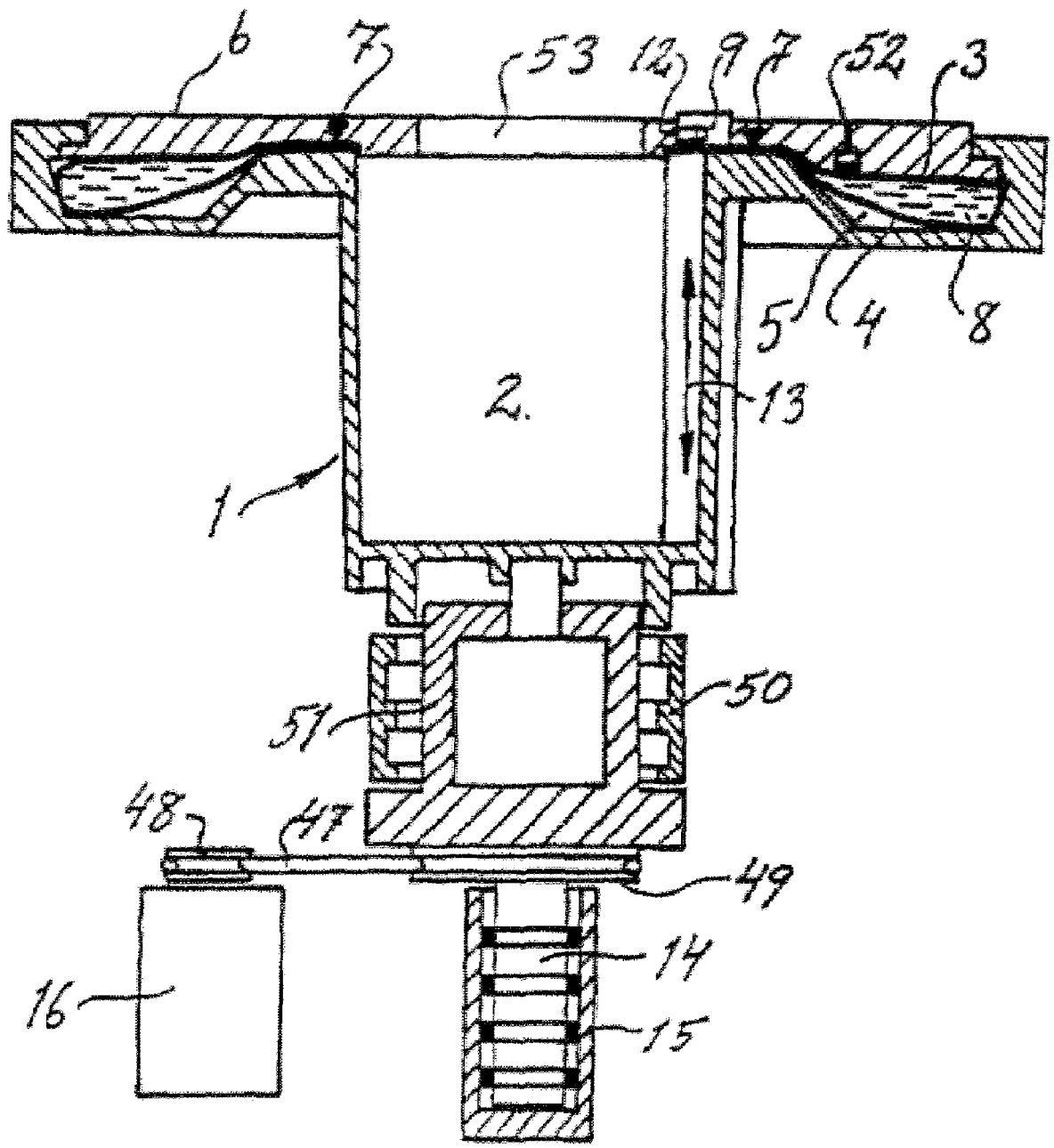
FIG. 1 a section through a typical centrifuge, in accordance with the invention FIG. 2 the ring bag intended for the centrifuge with the position of the section marked with line 1-1, in accordance with FIG. 1
Figure 2:
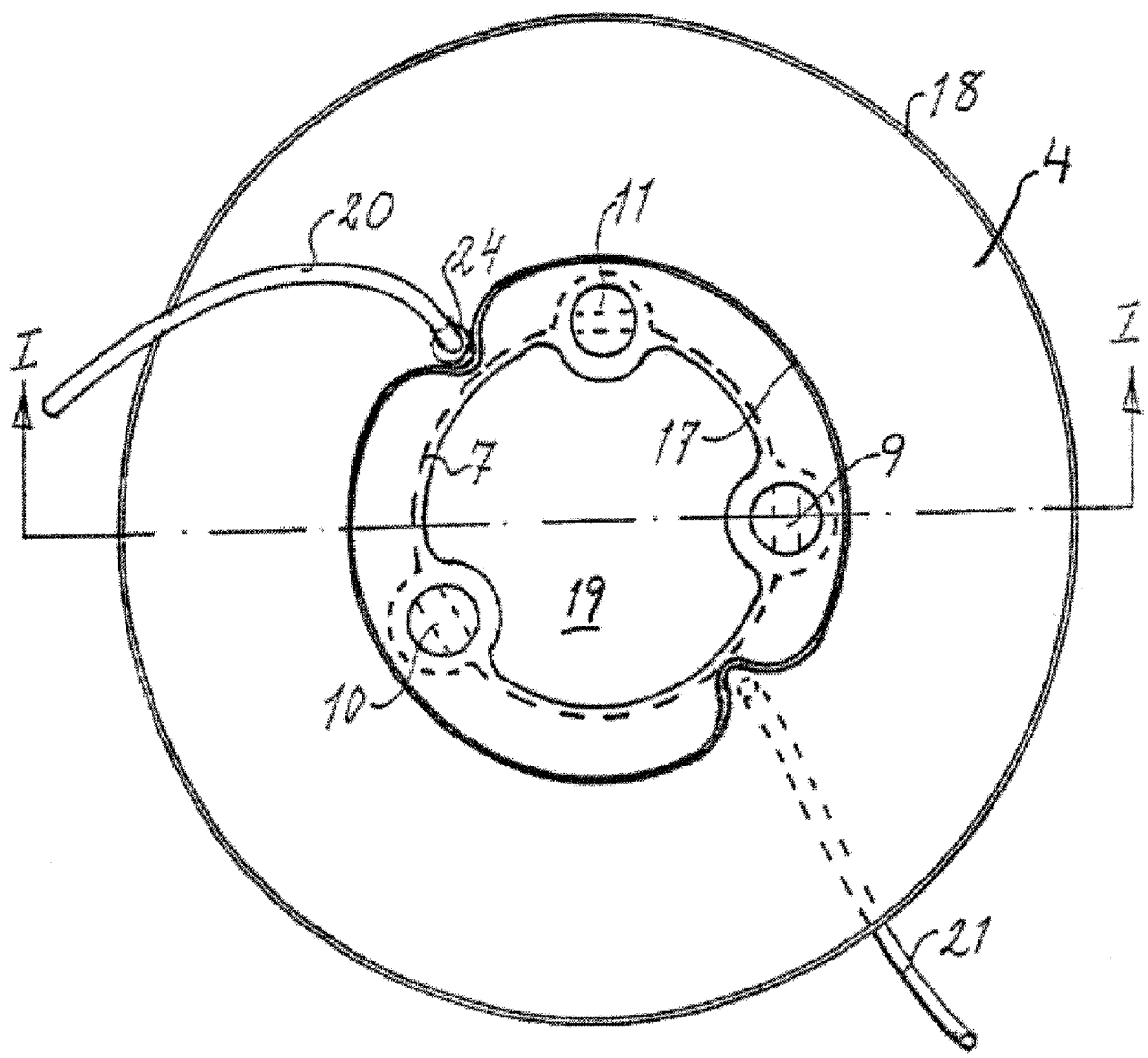

The centrifuge shown in FIG. 1 has rotor 1, centre chamber 2 where, for example, the final storage bags for the produced products can be located during the centrifuging operation while those connected to the same are filled with the desired component from the centrifuge's ring bag. Furthermore, ring chamber 3 is included for ring bag 4. In the latter the actual centrifuging operation is carried out. Beneath the ring bag and separated from it by a membrane is chamber 5 which can be filled with a hydraulic fluid with the purpose of exposing ring bag 4 to an external pressure for emptying the said ring bag. Centrifuge rotor 1 has furthermore a clockwise rotating lid 6 with the ring bag in which securing function 7 for ring bag 4 is built in. In FIG. 2 there is a dotted line 7 which illustrates where the clamping function affects the ring bag. In FIG. 1 ring bag 4 is drawn filled with fluid 8, which shall be centrifuged. In centrifuge rotor 1 there are three built-in supports 9-11. Of these only support 9 is shown on FIG. 1 but how the others internal position relates to this is shown in FIG. 2. In the supports, which have a primary function of defining ring bag 4's position in the centrifuge and holding the bags in position during centrifuging, guide groove 12 for different connecting tubes for the blood processing set can moreover be arranged. In these guide grooves the clamping function can be built in on the one hand, which makes them usable as a check valve for regulating the connection between the various parts of the bag sets and, on the other hand, as a welding function with which sealing and cutting of the same tubes can be carried out. Support 9 thus presupposes movement in arrow 13's direction and could therefore function as a clamp valve for the arranged tube in guide groove 12. The welding function on the supports requires access to electric power in the centrifuge rotor and, apart from that, requires contact lines between the rotor and centrifuge stand for the different control systems of the centrifuge. This has been brought about by means of slip ring connectors 14-15 between the rotor and stand where 14 marks the centrifuge's rotating part and 15 its included secured part in the centrifuge stand. On the figure the centrifuge motor is marked 16. This implies, as shown on the sketch, operating the centrifuge's rotor and by that means driving belt 47 located on the motor's driving pulley 48 and the centrifuge's driving pulley 49. The centrifuge's rotation bearing is marked 50 and the centrifuge's rotating guide is marked 51. Furthermore, in the centrifuge's inner lid there is a central opening 53 which makes centre chamber 2 accessible externally even when the inner lid is closed.

Ring bag 4 as shown in FIG. 2 consists of two sheets of some suitable plastic material joined together along the welded edges 17 and 18. Between the welded edges 17 and 18 the internally open ring chamber is formed, which is utilized during centrifuging. Besides ring welds 17 and 18 some welded points for strengthening around the holes which are intended for locating on supports 9-11. All the ring bags shown on the figures are formed with a central opening, which primarily corresponds to the centre chamber 2 opening. This is to simplify the passage to the centre chamber. On FIG. 2 this opening is designated 19. The ring bag shown in FIG. 2 has an opening for supports 9-11 as well as input and output tubes 20 and 21 attached to the ring bag's top and bottom sides by means of the welded sleeve couplings 24, i.e. securing parts in the form of a short piece of tube with a diagonally arranged flat securing collar which, in turn, is welded to the ring bag's top and bottom sides in which the connecting tubes in turn are secured by welding. Instead of being secured via a similar sleeve coupling the input and output tubes can also be secured to each respective welded edge, i.e. welding 17 and welding 18 on FIG. 2.

Figure 3:
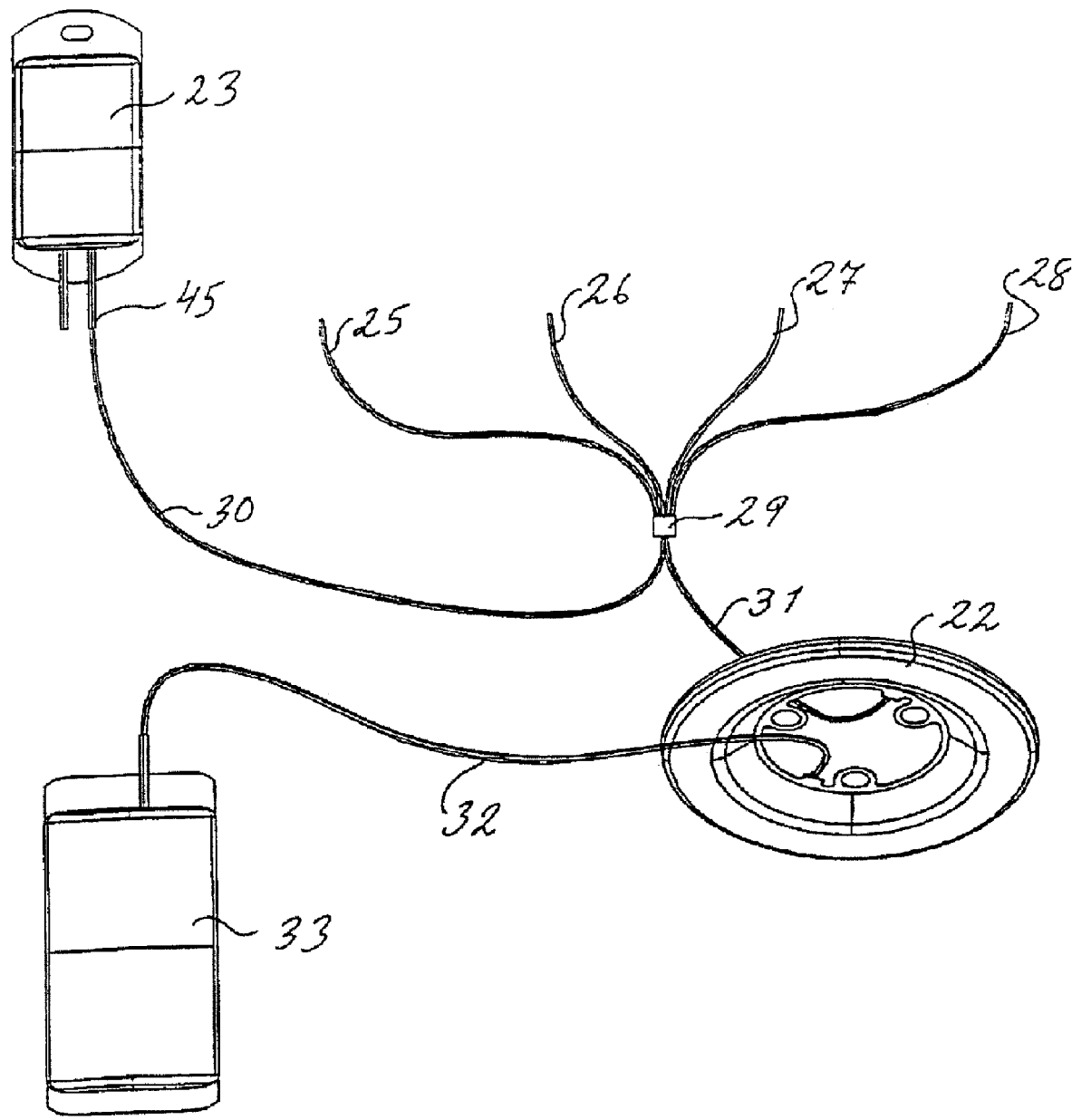
FIG. 3 bag set intended for blood platelet production from Buffy Coat

On FIG. 3 the bag set for producing blood platelets from the Buffy Coat consists of ring bag 22, a bag with diluting solution 23, four connecting tubes 25-28 (the number of connecting tubes can vary but, as a rule, should be between 4 and 6), with each one intended for welding to a bag with Buffy Coat, multi-way connector 29 which, on the one hand, via a tube 30 is connected to the diluting solution bag 23 and, on the other hand, to tube 31 and to ring bag 22. From the latter tube 32 is connected to final storage bag 33. In tube 30's connection to the diluting solution bag 23 there is blocking switch 45, which when required for starting the addition of diluting solution to the bags with Buffy Coat connected to tubes 25-28 can be opened by bending the tube. Before the blocking switch is opened connecting tube 30 shall be arranged in the guide groove 12 in one of the supports 9-11 that has the clamp valve function that is intended for controlling the addition.

Figure 4:
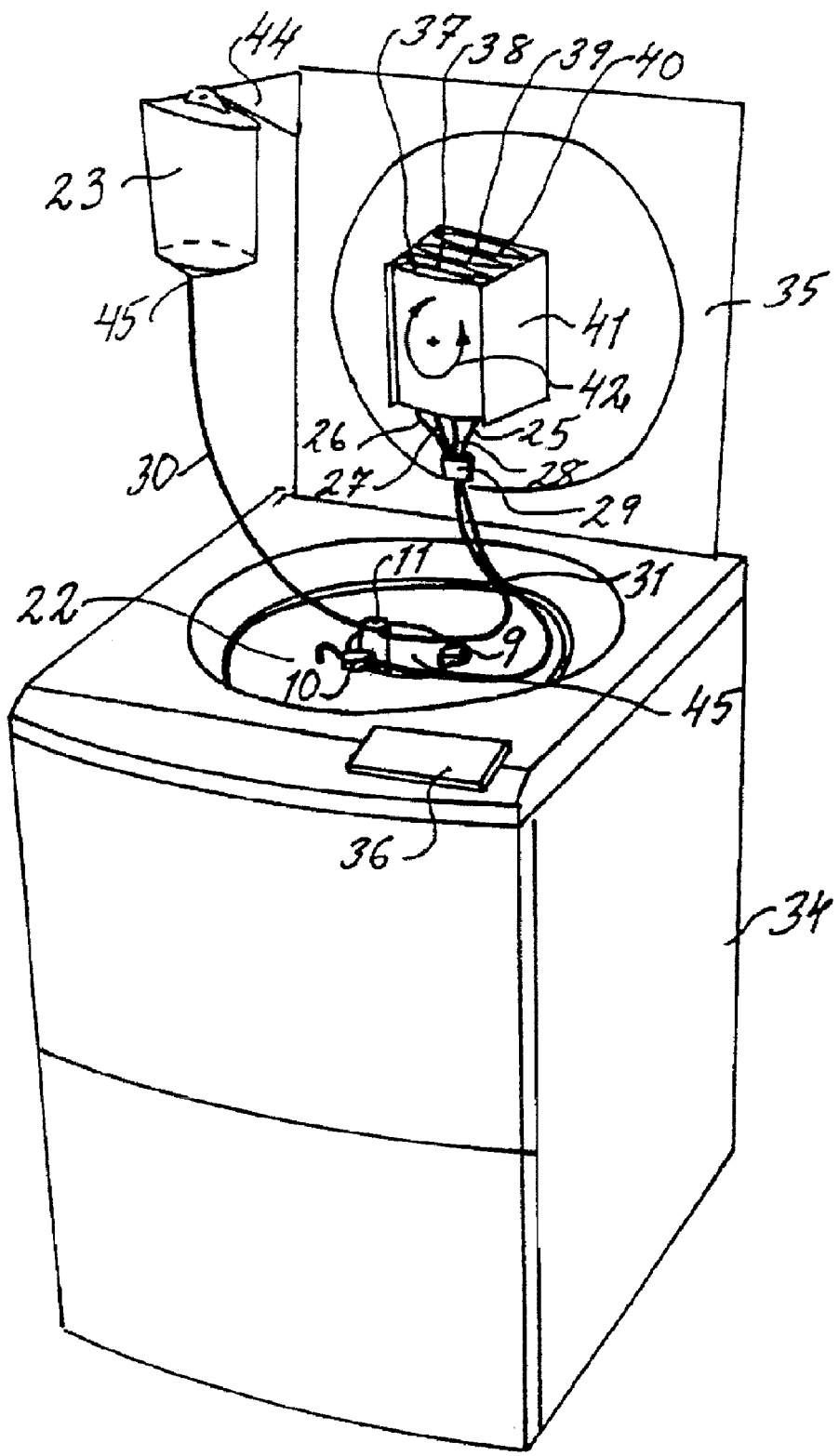
FIG. 4 centrifuge equipped with auto-pooling

As it is the particular bag set shown on FIG. 3 that is utilized in the method as shown in FIG. 4 we have retained the same designations, also in this figure even if the parts therein are drawn to a smaller scale and therefore also less parts. Otherwise, on FIG. 4 there is centrifuge 34 standing with its outer lid 35 completely open and locked in position. The centrifuge's inner lid has been omitted as it made the figure unclear when drawn. Also the centrifuge rotor and ring bag 22 has, to a certain extent, been drawn in a simplified manner. The centrifuge's control panel has been given the designation 36. Furthermore, the figure shows a position with four blood bags containing Buffy Coat 37-40 suspended in cassette 41, which is mounted on the inside of the centrifuge's outer lid. Blood bags 37-40 individual outputs have been connected, by sterile welding, to tube connectors 25-28 and the fluid content of the bags has, via the tubes and connecting tube 31 been transferred over into ring bag 22. After that, bags 37-40 have been supplied with washing fluid and diluting solution from diluting solution bag 23 suspended in holder 44. Diluting solution bag 23 is suspended sufficiently high above bags 37-40 to allow the diluting solution in sufficient amounts to be added to these bags as soon as blocking switch 45 in tube 30 and clamp valve in support 11, which tube 30 passes, are opened. Communication between bags 37-40 and ring bag 22 goes via tube 31 which in turn passes clamp valve in support 10 and with which the communication is controlled. After the addition of diluting solution in sufficient amounts to bags 37-40 the motor is started, not seen in connection with the cassette on the figure, and operates cassette 41 forward and backwards in a pendulum movement in accordance with curve 42 until all concentrate substance in the Buffy Coat bags is resolved and after that the built-in clamp valve in support 10 is opened, which output tube 31 from the multi-way connector 29 passes through and all substance added to ring bag 22 whereby tube 31, in support 10, is sealed by sterile welding and blocked after which the empty bags 37-40 and bag 23 with possible concentrates from the diluting solution can be rejected together with the tube system. The flushing out of the blood bags can, if required, be carried out in two or several consecutive flushing operations. After flushing out the blood bags, cassette 41 and holder 44 are removed from the centrifuge lid whereby the centrifuge is closed and centrifuging is carried out. Final storage bag 33 is located in the centrifuge's centre chamber 45. After centrifuging all blood platelet plasma is transferred to final storage bag 33 by the application to the bag of an external pressure which presses it together by adding hydraulic fluid to space 5 beneath the ring bag. Emptying the ring bag is interrupted by photocell 52 when it is registered that the interface between the desired lighter substance and the darker non-desired concentrate product is starting to approach the outlet through tube 32. After that tube 32 is sealed by sterile welding and sealed in one of the supports 9-11 after which the ring bag with non-desired concentrates of red blood cells, etc., can be rejected.

In addition, it can also be stated that an adapted database directly connected to a barcode reader is utilized to make all the processed blood products in the centrifuge, in accordance with the invention, directly traceable at the same time that the database also contains all the required control criteria for feasible blood product processing stages in the centrifuge.

What is claimed is:

1. A centrifuge for processing blood and blood components in a processing bag connected by a tube to at least one secondary bag, comprising
    a rotor for spinning the processing bag and separating a content thereof in at least two components;
    a means for exposing the processing bag to an external pressure and causing a transfer of a separated component from the processing bag into the at least one secondary bag,
    at least one electrically powered means mounted on the rotor for interrupting a transfer of fluid from the processing bag into the at least one secondary bag;
    a means for supplying electric power to the electrically powered means through the rotor; and
    a control means for enabling an effective program control of different functions in the rotor including at least one of a tube clamping function and a tube welding function.

2. A centrifuge according to claim 1, wherein the rotor comprises an axle and the electric power supply means comprises slip rings mounted on the axle of the rotor.

3. A centrifuge according to claim 1, wherein the at least one electrically powered means comprises at least one clamping means for closing or opening a tube connecting the processing bag to the at least one secondary bag.

4. A centrifuge according to claim 1, wherein the at least one electrically powered means comprises at least one welding means for sealing and cutting a tube connecting the processing bag to the secondary bag.

5. A centrifuge according to claim 1, wherein the at least one electrically powered means comprises at least one photocell for determining an interface between two components.

6. A centrifuge according to claim 5, wherein the rotor comprises a lid and the at least one photocell is included in the lid.

7. A centrifuge according to claim 6, wherein the lid clamps an inner edge of the processing bag when the lid is in a closed position.

8. A centrifuge according to claim 1, wherein the rotor comprises support means for engaging holes at a periphery of the processing bag and securing the processing bag to the rotor.

9. A centrifuge according to claim 8, wherein the support means are asymmetrically arranged on the rotor for positioning the processing bag in a determined position on the rotor.

10. A centrifuge according to claim 8, wherein the support means comprises a groove in which a tube can be engaged.

11. A centrifuge according to claim 8, wherein at least one support means includes a clamping means.

12. A centrifuge according to claim 8, wherein at least one support means includes a welding means.

13. A centrifuge according to claim 1, wherein the rotor comprises:
    a central chamber for at least one secondary bag; and
    a chamber for the processing bag, surrounding the central chamber; and
    wherein the means for exposing comprises:
    a hydraulic chamber which can be filled by a hydraulic fluid so as to expose a processing bag to an external pressure.

* * * * *